(12) United States Patent
McDevitt et al.

(10) Patent No.: US 9,709,580 B2
(45) Date of Patent: Jul. 18, 2017

(54) BIO-NANO-CHIPS FOR ON-SITE DRUG SCREENING

(75) Inventors: John T. McDevitt, Houston, TX (US); Nicolaos Christodoulides, Houston, TX (US); Pierre N. Floriano, Missouri City, TX (US); Glennon Simmons, Houston, TX (US)

(73) Assignee: William Marsh Rice University, Houston, TX (US)

( * ) Notice: Subject to any disclaimer, the term of this patent is extended or adjusted under 35 U.S.C. 154(b) by 444 days.

(21) Appl. No.: 14/114,925

(22) PCT Filed: Mar. 21, 2012

(86) PCT No.: PCT/US2012/030012
§ 371 (c)(1),
(2), (4) Date: Dec. 13, 2013

(87) PCT Pub. No.: WO2012/154306
PCT Pub. Date: Nov. 15, 2012

(65) Prior Publication Data
US 2014/0094391 A1    Apr. 3, 2014

Related U.S. Application Data

(60) Provisional application No. 61/485,189, filed on May 12, 2011.

(51) Int. Cl.
*G01N 33/94* (2006.01)
*G01N 33/53* (2006.01)
(Continued)

(52) U.S. Cl.
CPC .......... *G01N 33/948* (2013.01); *A61B 5/151* (2013.01); *A61B 10/007* (2013.01);
(Continued)

(58) Field of Classification Search
None
See application file for complete search history.

(56) References Cited

U.S. PATENT DOCUMENTS 6,589,779 B1    7/2003    McDevitt
6,602,702 B1    8/2003    McDevitt
(Continued)

FOREIGN PATENT DOCUMENTS

WO    2004009840    1/2004
WO    2005083423    9/2005
(Continued)

OTHER PUBLICATIONS

Jokerst et al., "Programmable Nano-Bio-Chip Sensors: Analytical Meets Clinical", Anal. Chem. 2010, 82:1571-1579, published online Feb. 3, 2010.*
(Continued)

*Primary Examiner* — Kaijiang Zhang
(74) *Attorney, Agent, or Firm* — Boulware & Valoir

(57) ABSTRACT

A bio-nano-chip (BNC) technology that works in connection with non-invasive samples, such as saliva, cheek swab or urine samples that can be easily performed by non-specialists, such as security personnel and police officers is disclosed. The microfluidic system for drug testing includes an analyzer or reader having a housing containing a slot for receiving a cartridge, a drug testing cartridge, a processor having a user interface, an optical or energy sensing means, and a means for moving fluid.

4 Claims, 5 Drawing Sheets

(51) Int. Cl.
    A61B 10/00      (2006.01)
    B01L 3/00       (2006.01)
    A61B 5/151      (2006.01)
    A61F 13/36      (2006.01)
    A61B 50/30      (2016.01)
    G01N 21/64      (2006.01)
(52) U.S. Cl.
    CPC .......... *A61B 10/0051* (2013.01); *A61B 50/30* (2016.02); *A61F 13/36* (2013.01); *B01L 3/5027* (2013.01); *G01N 33/946* (2013.01); *G01N 33/9486* (2013.01); *B01L 3/50273* (2013.01); *B01L 3/502715* (2013.01); *B01L 2200/027* (2013.01); *B01L 2300/0816* (2013.01); *B01L 2300/0867* (2013.01); *B01L 2400/0481* (2013.01); *G01N 21/64* (2013.01)

(56) References Cited

U.S. PATENT DOCUMENTS

| | | |
|---|---|---|
| 6,649,403 B1 | 11/2003 | McDevitt |
| 6,680,206 B1 | 1/2004 | McDevitt |
| 6,713,298 B2 | 3/2004 | McDevitt |
| 6,908,770 B1 | 6/2005 | McDevitt |
| 7,022,517 B1 | 4/2006 | McDevitt |
| 7,316,899 B2 | 1/2008 | McDevitt |
| 7,491,552 B2 | 2/2009 | McDevitt |
| 7,635,454 B2 | 12/2009 | Mastromatteo |
| 7,651,868 B2 | 1/2010 | McDevitt |
| 7,781,226 B2 | 8/2010 | McDevitt |
| 8,101,431 B2 | 1/2012 | McDevitt |
| 8,105,849 B2 | 1/2012 | McDevitt |
| 8,257,967 B2 | 9/2012 | McDevitt |
| 8,377,398 B2 | 2/2013 | McDevitt |
| 2004/0053322 A1 | 3/2004 | McDevitt |
| 2004/0132059 A1 | 7/2004 | Mastromatteo |
| 2005/0136548 A1 | 6/2005 | McDevitt |
| 2005/0233440 A1 | 10/2005 | Scurati |
| 2006/0073585 A1 | 4/2006 | McDevitt |
| 2006/0211059 A1 | 9/2006 | Taneja |
| 2006/0228256 A1 | 10/2006 | McDevitt |
| 2006/0257854 A1 | 11/2006 | McDevitt |
| 2006/0257941 A1 | 11/2006 | McDevitt |
| 2006/0257991 A1 | 11/2006 | McDevitt |
| 2008/0038738 A1 | 2/2008 | Weigum |
| 2008/0050830 A1 | 2/2008 | Floriano |
| 2008/0219891 A1 | 9/2008 | McDevitt |
| 2008/0286816 A1* | 11/2008 | Jehanli ............... G01N 33/558 435/7.92 |
| 2008/0300798 A1 | 12/2008 | McDevitt |
| 2009/0053733 A1* | 2/2009 | Link et al. ....... G01N 33/54326 435/7.1 |
| 2009/0215072 A1 | 8/2009 | McDevitt |
| 2009/0258791 A1 | 10/2009 | McDevitt |
| 2010/0291588 A1 | 11/2010 | McDevitt |
| 2011/0251075 A1 | 10/2011 | McDevitt |
| 2012/0208715 A1 | 8/2012 | McDevitt |
| 2013/0130933 A1 | 5/2013 | McDevitt |

FOREIGN PATENT DOCUMENTS

| | | |
|---|---|---|
| WO | 2005085796 | 9/2005 |
| WO | 2007002480 | 1/2007 |
| WO | 2012021714 | 2/2012 |

OTHER PUBLICATIONS

Cone et al., "Prevalence and Disposition of Drugs of Abuse and Opioid Treatment Drugs in Oral Fluid," J. Anal. Toxicol. 2007, 31:424-433.*
APS JK & Martens LC Review: The physiology of saliva and transfer of drugs into saliva, Forensic Sci Int 150: 119-131 (2005).
Christodoulides et al., Application of microchip assay system for the measurement of C-reactive protein in human saliva Lab. Chip, 5(3):261-9, 2005.
Blencowe T, et al, An analytical evaluation of eight on-site oral fluid drug screening devices using laboratory confirmation results from oral fluid, Forensic Science International 208:173-179 (2011).
Christodoulides N, et al., Lab on a chip Methods for Point of Care Measurements of Salivary Biomarkers of Periodontitis, Ann. N. Y. Acad. Sciences 1098:411-428 (2007).
Bosker WM & Huestis MA, Oral Fluid Testing for Drugs of Abuse, Clin. Chem. 55: 1910-1931 (2009).
Jesse V. Jokerst et al., Programmable Nano-Bio-Chip Sensors: Analytical Meets Clinical, Analytical Chemistry, vol. 82, No. 5, Mar. 1, 2010.
Choo RE, Huestis MA. Oral fluid as a diagnostic tool, Clin Chem Lab Med 42(11):1273-1287 (2004).
Cone EJ, Saliva testing for drugs of abuse, Ann N Y Acad Sci 694:91-127 (1993).
Drummer OH, Introduction and review of collection techniques and applications of drug testing of oral fluid, Therapeutic Drug Monitoring 30: 203-206 (2008).
Drummer OH, Review: Pharmacokinetics of illicit drugs in oral fluid, Forensic Science International 150: 133-142 (2005).
Floriano PN, et al. Use of saliva-based nano-biochip tests for acute myocardial infarction at the point of care: a feasibility study, Clin Chem. 55(8):1530-38 (2009).
Pehrsson et al., An evaluation of on-site oral fluid drug screening devices DrugWipe 5+ and Rapid Stat using oral fluid for confirmation analysis, J. Anal. Tox., 35(May): 211-218 (2010).
Idowu OR & Caddy B, A Review of the Use of Saliva in the Forensic Detection of Drugs and Other Chemicals. J Forensic Science Society 22: 123-135 (1982).
Jokerst JV, et al. Nano-bio-chips for high performance multiplexed protein detection: Determinations of cancer biomarkers in serum and saliva using quantum dot bioconjugate labels, Biosens Bioelectron. 24:3622-29 (2009).
Kaufman E & Lamster IB, The diagnostic application of saliva—A review, Crit Rev Oral Biol Med 13: 197-212 (2002).
Lillsunde P, Analytical techniques for drug detection in oral fluid, Therapeutic Drug Monitoring 30: 181-187 (2008).
Melanson Sef, Drug-of-Abuse Testing at the Point of Care, Clinics in Laboratory Medicine 29: 503 (2009).
Riet DR, et al., Oral Fluid as an Alternative Matrix to Monitor Opiate and Cocaine Use in Substance-Abuse Treatment Patients, Drug Alcohol Depend, 87(2-3): 258-267 (2007).
Rifai N & Ridker PM, High-Sensitivity C-Reactive Protein: A Novel and Promising Marker of Coronary Heart Disease, Clin Chem 47: 403-411 (2001).
Scheidweiler KB et al., Pharmacokinetics of Cocaine and Metabolites in Human Oral Fluid and Correlation With Plasma Concentrations After Controlled Administration. Ther Drug Monit 32(5): 628-637 (2010).
Schramm W, et al., Drugs of Abuse in Saliva—a Review, J Analytical Toxicology 16: 1-9 (1992).
Svojanovsky SR, et al., High sensitivity ELISA determination of taxol in various human biological fluids, J Pharm Biomed Anal 20: 549-555 (1999).
Toennes SW, et al., Driving under the influence of drugs—evaluation of analytical data of drugs in oral fluid, serum and urine, and correlation with impairment symptoms, Forensic Sci Int 152: 149-155 (2005).
Van Bocxlaer JF, et al., Liquid chromatography-mass spectrometry in forensic toxicology, Mass Spectrometry Reviews 19: 165-214 (2000).
Walsh JM, et al., An evaluation of rapid point-of-collection oral fluid drug-testing devices, J Anal Toxicol 27: 429-439 (2003).
Yeh CK, et al., Current development of saliva/oral fluid-based diagnostics, Tex Dent J. 127(7):651-61 (2010). Review.
Preston et al., Comparison of self-reported drug use with quantitative and qualitative urinalysis for assessment of drug use in treatment studies, NIDA Research Monograph 167 (1997): 130-45.

(56) References Cited

OTHER PUBLICATIONS

Yamaguchi et al., A rapid enzyme immunoassay for cocaine and benzoylecgonine using glucose oxidase, J. Health Sci., 47(4) 419-423 (2001).
Niedbala et al., Immunoassay for detection of cocaine/metabolites in oral fluids, J. Anal. Tox., 25 (Jan./Feb.): 62-68 (2001).

* cited by examiner

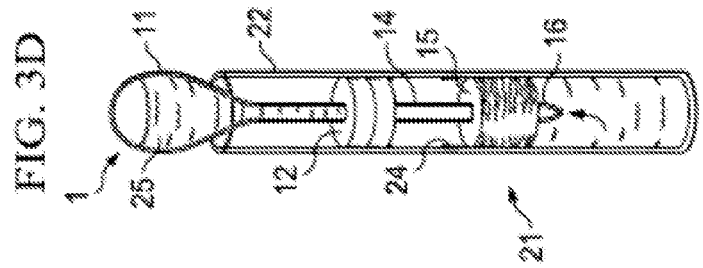
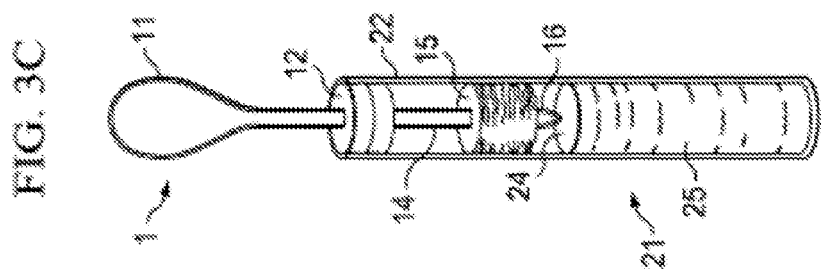
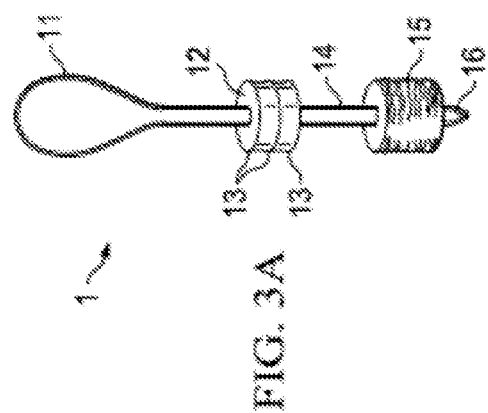
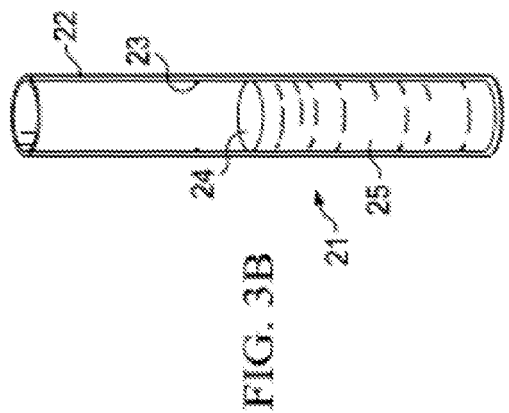

US 9,709,580 B2

BIO-NANO-CHIPS FOR ON-SITE DRUG SCREENING

PRIOR RELATED APPLICATIONS

This application is a National Filing under 35 U.S.C. §371 of International Application PCT/US12/30012, filed on Mar. 21, 2012, which claims priority to U.S. Ser. No. 61/485,189, filed May 11, 2011. Each of these patent applications is incorporated by reference in its entirety.

FEDERALLY SPONSORED RESEARCH STATEMENT

Not applicable.

FIELD OF THE INVENTION

The invention relates to microfluidic devices, systems, methods and kits for drug testing, that is reliable, fast and simple enough to use even in a security or employment settings.

BACKGROUND OF THE INVENTION

Current testing of biological samples for drugs of abuse is limited by the complexity of the lab-based tests and the challenges associated with sample collection. Complicated lab instrumentation and difficult sample preparation has limited access to convenient sample testing. There are also challenges with respect to gathering both blood and urine samples. For blood, there is a requirement of venipuncture and the necessity of having access to a phlebotomist. For urine, there is a problem with chain of custody and the potential for sample adulteration.

Thus, what is needed in the art is a simple, yet reliable and sensitive method of obtaining biological samples and testing same for drug content, that can be used in any setting, including road-side, police stations, airports, and work or school environments. Such a test would be a tremendous benefit in law enforcement and sensitive security situations.

SUMMARY OF THE INVENTION

The technology here described employs bio-nano-chip (BNC) technology that works in connection with non-invasive samples, such as saliva, cheek swab or urine samples that can be easily performed by non-specialists, such as security personnel and police officers. Further, the mini-sensor ensemble here described is unique in its capacity to provide lab quality data at the point of need without extensive sample processing. Further, the tests have a lower limit of detection of less than 10 ng/ml, and in some cases less than 1 ng/ml, and a detection range covering at least four orders of magnitude and in some cases five orders.

The BNC device employs optical bead sensor technology to analyze biological samples, such as saliva, for the presence of drugs of abuse. The BNC-based tests are applied for the detection and measurement of drugs of abuse in biological specimens collected by non-invasive (i.e. saliva or urine) or minimally-invasive (i.e. finger-stick blood) sampling approaches. The drug screening device or 'drug-ometer' is programmed to execute a number of 2-10 minute tests, which will reveal if there are any drugs, and at what levels, present in the body.

In more detail, the invention is a microfluidic system for drug testing comprising an analyzer or reader having a housing containing a slot for receiving a cartridge, a drug testing cartridge, a processor having a user interface, an optical or energy sensing means, and a means for moving fluid. In a preferred embodiment, the housing also contains heating and cooling means, such as piezoelectric heater/cooler, radiant heater and fan, peltier, and the like. The optical sensing means is configured to receive a signal from said bead sensors, and the microfluidics are configured so as to allow fluid movement past said bead sensors. The processor and user interface control the system and the processor records data from said optical sensing means. Also preferred is device that includes a display means operably connected to said processor for displaying said data, but the display means is optional, and a data-port can instead connect to independent processors and/or display means.

Any commercially available reader can be used, or the reader can be manufactured specially for the test. Commercially available readers to date include the Agilent™ 2100 bioanalyser; LabChip® EZ Reader; VereID™ Biosystem; Micro Total Analysis System (μTAS); Analyzer™, and the like, but we envision that a dedicated device will be manufactured to be specific for this application, thus minimizing the size and complexity of the device, while maximizing ease of use.

In other embodiments, the invention is a cartridge comprising a substrate having inlets and microfluidics for moving fluid and a plurality of individual bead sensors wherein each bead sensor is a porous polymeric bead having a competitor drug bound thereto (either covalently bound or just absorbed, adsorbed, or adhered thereto).

The cartridge or card can also include blisters containing reagent fluids for use in said system. The reagents include wash buffers, reaction buffers, and the like, and can also include an anti-drug antibody coupled to a signaling reagent (i.e. tracer). The signaling reagent can be any reagent capable of providing a signal to the optical or energy sensing means, and preferably are fluorescent dyes, radioactive reagents, phosphorescent, chemi-luminescent or other energy emitting reagents. The analyzer can thus include mechanical actuators that apply pressure for the bursting of the blisters in a controlled fashion for the delivery of the said buffers and reagents.

In other embodiments, the invention is the cartridge as described above, which can also include internal microfluidics on said substrate for carrying fluid to and from said bead sensors, as well as sample and/or fluid entry/exit port(s), together with a valve or access port, e.g., a pinch valve or elastomeric stopper for accessing said internal microfluidics.

The invention also includes drug testing methods, using the cartridge and device of the invention. Preferably, a sample is provided by using a simple swab taken from the mouth, which is then inserted in the lab card/analyzer for drug measurement. Alternatively, the same method may be used in conjunction with needle-prick derived whole blood or urine. The sample is applied to the cartridge, which is then inserted into the slot, fluids are applied, signal is generated and the data is read and displayed either on the device or an independent display means.

In more detail, one embodiment of the invention disposable drug testing cartridge comprising a generally flat substrate having thereon individual bead sensors arranged in an array, wherein each bead sensor is a porous polymeric bead having a drug bound thereto, wherein said drug is selected from 3, or more of tetrahydrocannabinol (THC), diazepam, oxazepan, nordiazepam, temazepam, D-amphetamine, methamphetamine, methadone, morphine, cocaine, 3,4-

Methylenedioxyamphetamine (MDA) 3,4-Methylenedioxymethamphetamine (MDMA) and biological metabolites of same. The cartridge can also contain 4, 5, 6, 7, 8, 9, 10, 11, 12 or more of said drugs, and/or additional drugs can be added to the test and cartridge.

Preferably, the cartridge also has internal microfluidics on said substrate for carrying fluid to and from said bead sensors, and a sample entry port. In some embodiments, the drug testing cartridge can include at least one reagent blister fluidly connected to said bead sensors, and/or at least one waste fluid chamber fluidly connected to and downstream of said bead sensors. However, in other embodiments, these can be provided by the analyzer.

Preferably, the drug testing cartridge has positive and negative control bead sensors and calibrator bead sensors, and every drug bead sensor is present in said array in at least duplicate or triplicate or more.

Preferably, each bead sensor is a porous polymeric bead of size between 50-300 nm±10% having a drug conjugated thereto. Usually, the drug is conjugated to said bead sensor via a linker, but this can vary depending on the bead sensor chemistry. Preferably, the bead sensor comprises crosslinked agarose, and the linker is a peptide or protein, such as BSA.

In one embodiment, the disposable drug testing cartridge can include reagent chambers, one of which contains an absorbent pad containing dried antibodies for said drugs, each antibody conjugated to a fluorophore. Another reagent chamber can contain wash buffer.

In another embodiment, the invention is a lab-on-chip system for drug testing comprising a analyzer having a housing containing i) a slot for receiving a cartridge, ii) a processor having a user interface, iii) an optical or energy sensing means, and iv) a means for moving fluid. The analyzer is used with a cartridge as described above, wherein said cartridge fits into said slot such that said inlets are fluidly connected to said means for moving fluid, the optical sensing means is configured to receive a signal from said bead sensors, the microfluidics are configured so as to allow fluid movement past said bead sensors, and the processor and user interface controls said lab on chip system and said processor records data from said optical sensing means. Preferably, the processor uses line profile and/or circular area of interest to analyze said data.

The invention can also be a kit comprising the cartridge as described above, wrapped in an airtight package, together with a vial of wash buffer, and a swab or other sample collection device, instructions and the like. A sample collection and solubilization device can comprise a container closed with a cap, a lower portion of said container having a buffer separated from an upper portion of said container by a piercable membrane, and the cap comprising a flexible bulb passing through said cap and fluidly connected to a hollow stem ending in a point, a lower portion of said stem being coated with an absorbent or bristled material for collecting a biological sample, wherein said device is proportioned to store said cap with said stem and said swab in said upper portion of said container, but can reach said buffer when said point pierces said piercable membrane, and said flexible bulb can be used to draw up and deliver said buffer.

As used herein, "embedded" channel or chamber, what is meant is that the channel or chamber is enclosed inside the substrate, rather than being an open top channel or chamber on the surface of the substrate. Embedded channels and chambers can be made in lab cards, as described in US20040132059, US20050233440 and U.S. Pat. No. 7,635,454, or can be made by welding patterned layers together.

By "reader" or "detector" or "analyzer" what is meant is a device that contains the optics, optic sensing means, processor, user interface, and fluidics and is the device that runs the assays described herein and thus "analyzes" the sample and "reads" or "detects" the results.

By "card" or "cartridge" what is meant is a generally planar substrate having microfluidic channels and chambers therein, as well as one or more access ports, and houses the bead array specific for the drug testing assays described herein.

By "reverse competitive assay" what is meant is a competitive immunoassay, wherein the target is immobilized, rather than the antibody. Thus, as described herein, the targets are bead bound, and the labeled antibody is in the assay solution. Drug presence in the sample reduces the signal as in the typical competitive assay.

By "label" what is meant is any detectable chemical, but preferably including a bioluminescent, chemi-luminescent or fluorescent molecule.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as various buffers, differing salts, extra wash or precipitation steps, pH modifiers, and the like.

The following abbreviations are used herein:

| Abb. | Name |
| --- | --- |
| Ab | Antibody |
| AMPH | Amphetamine |
| BSA | Bovine serum albumin |
| BZE | Benzoylecgonine |
| BZO | Benzodiazepine |
| cAOI | circular area of interest |
| CP | circular profile |
| CTL | Control |
| % CV | % coefficient of variation |
| fAOI | fixed AOI |
| ICS | Immunochromatographic strip |
| ID | integrated density |
| IFA | Immunoformat A (drug on bead) |
| IFB | Immunoformat B (MAb on bead) |
| LC-MS/MS | Liquid chromatography tandem mass spectroscopy |
| LOC | Lab on chip |
| LOD | Limit of Detection |
| LOQ | Limit of Quantitation |
| LP | Line profile |
| MAb | Monoclonal antibody |
| MDA | 3,4-Methylenedioxyamphetamine |
| MDMA | 3,4-Methylenedioxymethamphetamine |
| METH | Methamphetamine |
| PBS | Phosphate buffered saline |
| SI | signal intensity |
| THC | Tetrahydrocannabinol, aka delta-9-tetrahydrocannabinol (Δ9-THC), or dronabinol |

DESCRIPTION OF THE DRAWINGS

FIG. 3A-D show top or cap 1 in FIG. 3A and vial 21 in FIG. 3B. They are shown in a storage configuration in FIG. 3C and in a wash configuration in FIG. 3D.

EXAMPLE 1

Proof of Concept

Figure 1B:
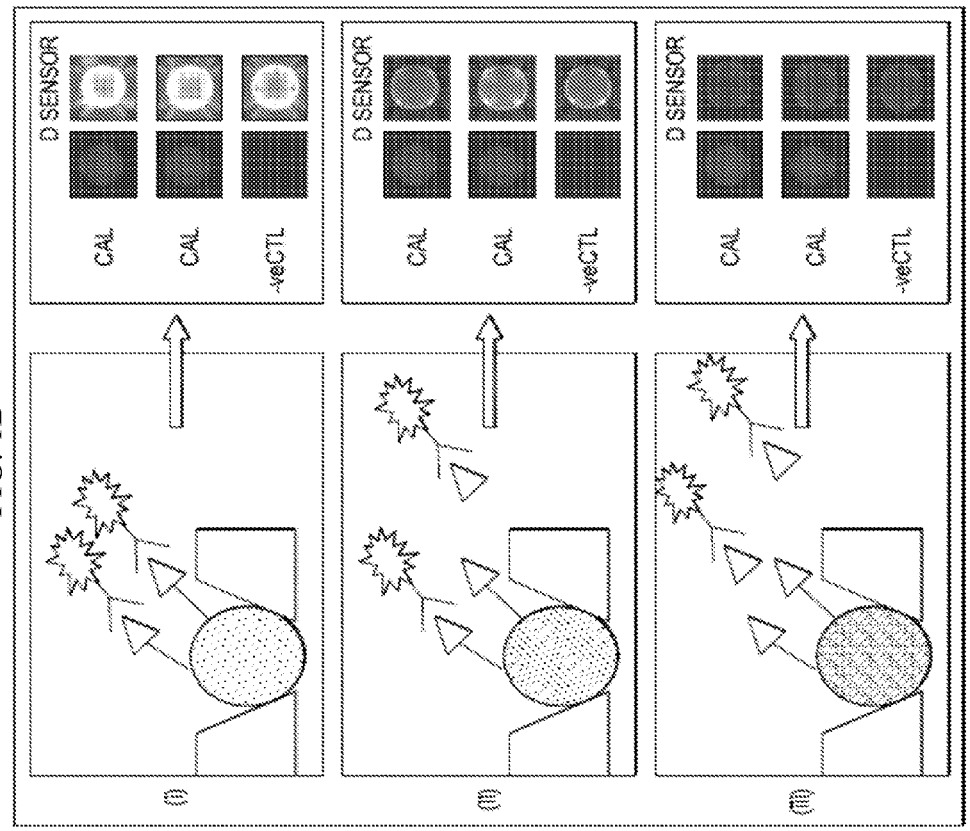
FIG. 1A-B: (A) Components and (B) reverse competitive immunoassay scheme and typical result of competitive-type BNC drug test immunoassay demonstrating a dose-dependent (i—control 0, ii—10 and iii—100 ng/mL amphetamine, respectively) decrease in the fluorescent signal gathered on beads sensitized for the target drug. Note the dose-dependent decrease in signal acquired on the drug sensors (D sensor), the absence of signal on negative control beads (−ve CTL) and the consistency in signal intensity on the calibrator beads after the 3 assay runs.
Figure 1A:
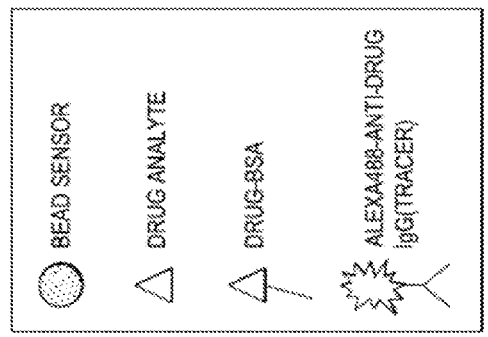

Reverse Competitive Immunoassay: Bead-based drug-specific tests were developed as reverse competitive immuno-assays (FIG. 1). The assay sequence included addition of the sample to an anti-drug specific tracer antibody solution and delivering the mixture to an array of addressable beads. The array included beads coupled to BSA-drug conjugates (drug sensors), beads coated with BSA alone (that serve as negative controls and indicators of the specificity of the reactions that take place within the lab card), as well as beads loaded with fixed amounts of photo-stable fluor that serve as calibrators of the LOC system. The array also offers a bead redundancy that contributes to higher accuracy and precision of LOC drug measurements.

In the absence of drug in the sample, the tracer antibody (a labeled antibody) specifically bound the drug sensors and produced a strong signal on the surface as well as within the interior of the porous bead. In the presence of drug in the sample, the binding of the tracer was reduced in a drug specific, dose-dependent manner. Use of drug standards allowed for the generation of dose response curves, which were then be used to interpolate the concentration of the drug in unknown samples. In the example shown in FIG. 1, representative images of the bead array exposed to 0, 10 and 100 ng/mL of amphetamine are shown.

The reverse competitive immunoassay has at least three advantages. First, it is easier to bind the fluor to the antibody than to the drug. Secondly, the assay needs only a single labeled antibody per drug. Lastly, the tests are more sensitive or can detect lower levels of drugs when set up this way.

Bead Sensor Development: Macro beads were used in the proof of concept studies as easy to make and handle. Beads were developed as described previously (Christodoulides, Ann. N.Y. Acad. Sciences 1098:411-428 (2007)).

Past research with bead sensors consistently revealed that the precision of the assays was highly dependent on their size homogeneity. Accordingly, an integral component of the bead production protocol included a sieving step where beads within a 280±10 μm diameter distribution were selected. Thus, beads should be sorted to obtain a narrow size range, preferably ±10% or more preferred ±5% or less.

Some outlier beads do occasionally appear in the array. However, because of the bead redundancy associated with this approach (at least 4 beads dedicated for each bead type) in conjunction with the application of automated image analysis macros that can identify and, thus, exclude the outlier beads based on established outlier removal routines, such as median tests, Grubbs, or Dixon tests from the statistical analysis that are embedded in the data analysis modules, we can achieve assays with excellent intra- and inter-assay precision (typically at 5-10% CV and 3-10% CV, respectively). Preliminary evaluation of the precision of the drug-specific tests we developed for this program showed intra-bead % CV between 2-12%.

Reagents were selected after considerable testing for sensitivity, specificity and reliability. The reagents used in these proof of concept assays are listed in

TABLE 1

| Reagents | | |
|---|---|---|
| Reagent | Company | Catalogue Number |
| THC-BSA | Arista Biologicals, Inc. | AGTHC-0304 |
| Cocaine-BSA | Pyxis Laboratories Inc. | N/A: cocaine-BSA |
| Diazepam-BSA | Arista Biologicals, Inc. | AGBZO-0306 |
| D-amphetamine-BSA | Arista Biologicals, Inc. | AGAMP-0315 |
| Methamphetamine-BSA | Arista Biologicals, Inc. | AGMET-0300 |
| Anti-THC antibody | Randox/Bioventix | BVX.THC.2B9 |
| Anti-cocaine antibody | Pyxis Laboratories Inc. | AC6029A |
| Anti-diazepam antibody | Arista Biologicals, Inc. | ABBZO-0400 |
| Anti-D-amphetamine antibody | Arista Biologicals, Inc. | ABAMP-0400 |
| Anti-methamphetamine antibody | Arista Biologicals, Inc. | ABMET-0400 |

BSA-drug conjugates were coupled to the agarose bead sensors using reductive amination. Briefly, 500 μL volume of beads were rotate-incubated overnight with BSA-drug conjugates in the presence of a fixed concentration of sodium cyanoborohydride in a round bottom eppendorf tube hosting a total reaction volume of 1500 μL. The following day, the beads were allowed to settle, the supernatant was aspirated and beads were washed two times with PBS. This was followed by 1 hour blocking step with 50 mM Tris buffer and freshly prepared solution of sodium cyanoborohydride, followed by a final two washes with PBS.

Conjugation of BSA-drug was confirmed by staining beads with coomasie blue and conjugation efficiency quantitatively determined through spectrophotometric comparison of representative samples collected before and after the conjugation. A similar protocol was used to create a large supply of calibrator beads (beads conjugated to a fixed concentration of AlexaFluor®-488-conjugated antibody irrelevant to the drug targets), as well as negative control beads conjugated to BSA alone. All bead conjugates were stored in PBS at 4° C. until use.

Development of Drug-Specific Tracers: Conjugation of Alexa Fluor® 488 dye to anti-drug antibodies to create the tracer reagents for the competitive immunoassays was completed as described in the manufacturer's manual (Cat.# A-10235, Alexa Fluor® 488 Protein Labeling Kit, Invitrogen). The Alexa Fluor® 488 dye, which is spectrally similar to fluorescein, produces protein conjugates that are brighter and more photostable than fluorescein conjugates. In addition, unlike fluorescein, the fluorescence of the Alexa Fluor® 488 dye is insensitive to pH between pH 4 and 10. Alexa Fluor® 488 dye-labeled proteins have absorption and fluorescence emission maxima of approximately 494 nm and 519 nm, respectively meeting the optical specifications of the fluorescence-based analyzer.

Data Collection: BNC based assays were performed at room temperature under continuous fluid flow conditions using a prototype lab-on-chip system. In brief, the system uses a commercial card reader called Analyzer™ and lab assembled cartridges containing an array of bead sensors, with two reagent blisters containing buffer with microfluidic channels connecting same. The bead sensors were arrayed by placing the beads onto a bead holder with forceps (tweezer). The bead holder includes an array of wells, each of which hosts a single bead in addressable position within the array; the array dropped into a slot or recess in the cartridge for same.

The total assay time was 10-12 minutes. This included the sequential priming of the microfluidic lines, delivery of the tracer/sample mixture to the array of bead sensors and a final wash with PBS.

After each assay run, photomicrographs of the bead array were captured at various charged coupled device (CCD) exposure settings. The Analyzer™ instrument was equipped with various excitation filters, which can be selected as needed depending on which label is selected for detection, and include red, blue and green signals.

The images were saved as 24-bit colorized TIFF files and analyzed via NIH ImageJ software (Bethesda, Md.) with bead fluorescence signal intensity inversely correlating to the concentration of drug/analyte in the sample.

Data Analysis: Customized macros were developed and optimized for the automated analysis of drug-specific bead-based assays serve to determine the exact bead location, followed by their respective bead-specific assignments and to extract bead data using 5 different "regional pixel extraction-analysis" strategies that can be automatically applied for the generation of dose response curves as well as used for the measurement of the various drug levels in unknown samples.

Figure 2:
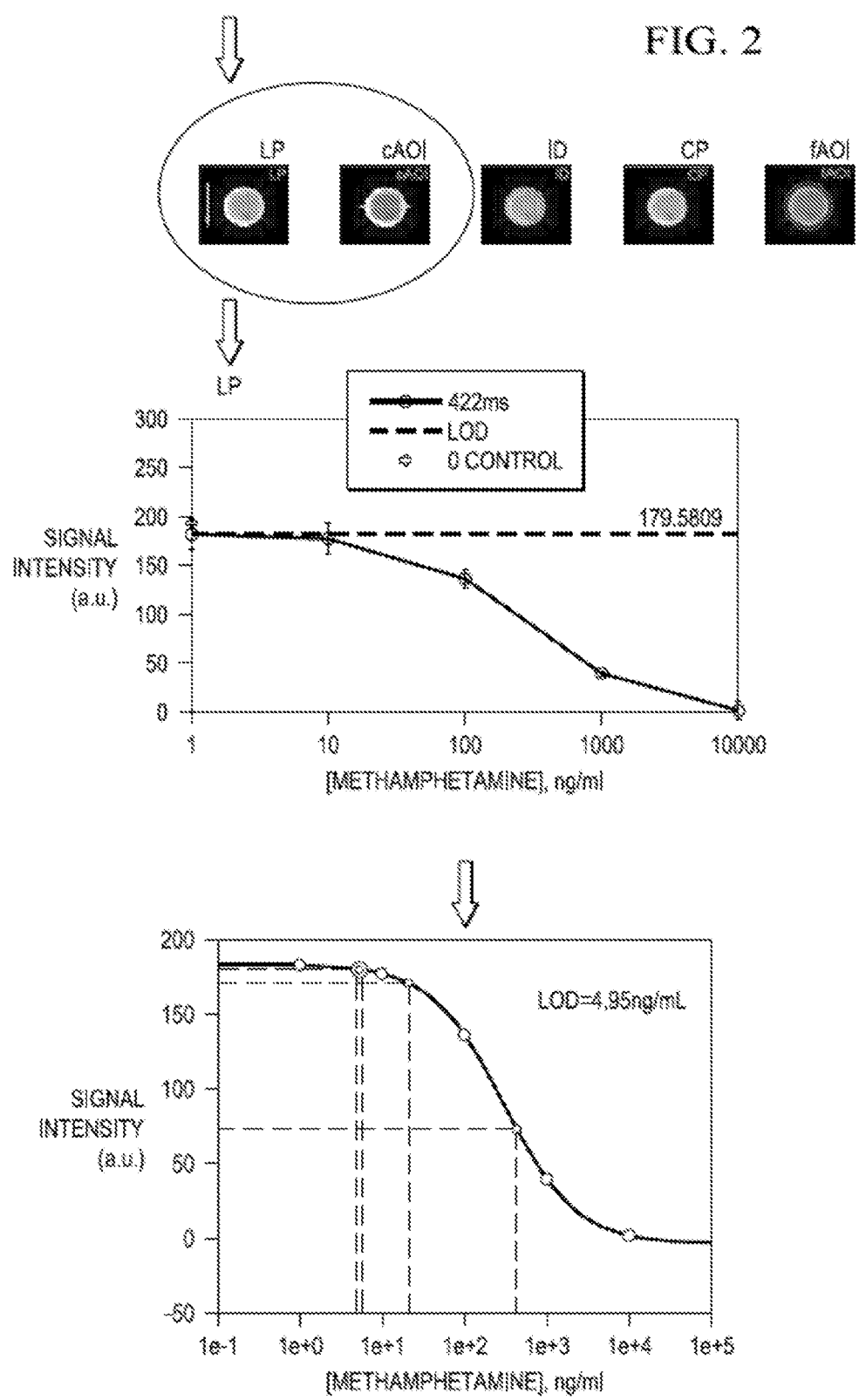
FIG. 2. Bead image analysis methods: Line profile (LP), circular area of interest (cAOI), integrated density (ID), circular profile (CP) and fixed AOI, for the generation of dose response curves for NBC-based assay for THC. Each bead from the array was probed with these different data analysis strategies. Dose response curves generated by each method were compared and the method, or combination of methods, that provided the most sensitive and wide detection capabilities were selected as the optimal image analysis approach for subsequent experiments. Line profile and circular area of interest were the most informative data analysis method, and exemplary data for the LP analysis is shown in graphic form on the bottom. 422 ms is the exposure time of the CCD (camera) of the optical sensor. The dotted line on the left graph is the threshold signal intensity that defines the LOD for this assay. The threshold signal intensity (179.58) is defined by the signal intensity of the zero drug condition (i.e. +0 CONTROL) minus 3× times the standard deviation of the same zero drug standard run. The threshold signal intensity is then applied on the graph on the right. It is plotted as SI (large dot) and interpolated from the graph on the right to provide the LOD of 4.95 ng/mL for this assay (X-axis, see dashed line). The other dotted lines are results from the testing of unknown samples.

The assays benefited from automated image and data analysis macros developed specifically for this application (FIG. 2). Five dedicated image analysis "probing" strategies are shown in FIG. 2, including Line profile (LP), circular area of interest (cAOI), integrated density (ID), circular profile (CP) and fixed AOI.

The algorithm compiled results for each bead, statistical analysis with exclusion of outliers within each group of beads and output log files with the average, standard deviation and coefficient of variance for each group that can be inserted and further processed into a Microsoft Excel environment. Intensity versus concentration calibration curves were constructed with best-fit regression analysis for determination of unknown sample concentration. Data obtained from the testing of drug standards and zero antigen controls were then entered and processed to derive the dose response curves, as well as assay characteristics such as limit of detection, assay range and precision.

The dose response data as well as data obtained from the testing of samples were entered into unknown prediction equations according to standard curves obtained for each analyte on the system to determine the drug concentrations. Further enhancement in data quality was obtained by using image acquisition with various exposure times. The latter feature was developed with the flexibility that allows selective independent analysis for each assay using the optimal integration time for each target drug under the various conditions tested.

Line Profile (LP) and circular Area of Interest (cAOI) were the two image analysis methods that consistently provided the best results. Hence, these two methods were selected and used extensively for the validation of the drug tests with respect to assay performance studies.

For the Line Profile, a series of lines going through about 80% of the beads were profiled for the maximum intensities (or maxima). Because the signal is typically lower at the center of the beads, the product of a line profile is typically two maxima at the edge of the bead. All measurements were averaged and outliers identified and removed according to well established non-proprietary outlier removal routines (median, Grubb's, or Dixon tests).

For circular Area of Interest, a series of concentric areas centered on the center of the beads, and starting with a diameter of only a few pixels are drawn with increasing radii. For each of these circular areas, the average intensity per pixel was calculated and the circle was increased until it has exceeded the size of the bead by 10%. The maximum signal obtained typically at the bead periphery can be determined from the highest circular area value.

Assay Performance: The LOD, LOQ, detection range and dynamic range (range of quantitative data) for each drug-specific assay on the LOC system were established as follows: The assay dilution buffer was processed in the absence of antigen to establish the mean signal intensity on the drug sensor beads for the zero-analyte condition (baseline) in response to the tracer. The standard deviation from bead to bead of the zero-analyte condition was recorded and used to derive a threshold signal intensity (SI) value using the signal intensity of the drug-sensitized beads minus 3× standard deviations for the "zero" drug condition. The assay was then repeated with increasing concentrations of drug standard antigen added in each run and signal intensities for the drug sensor beads within the array for each concentration were averaged and recorded.

The LOD for this competitive type of assay was defined as the lowest concentration of antigen standard that yields an average bead signal lower than the threshold SI value. The detection range of the assay was defined by its LOD at the low end of analyte concentrations and by the drug concentration that caused the ultimate level of decrease in the signal. The mean signal intensity from the analyte-specific beads was then plotted against the analyte concentration to establish the dose-response curve for the given assay. The LOQ was determined as the lowest drug standard concentration on the linear portion of the dose-response curve (~10 sd below the SI from the zero condition); the LOQ together with the lower end of the linear portion of the curve were used to establish the quantitative range (also known as useful range or dynamic range) of the assay.

FIG. 2 provides a typical dose response for the drug methamphetamine, but the other dose response curves are omitted for brevity. Instead, the complete assay performance characteristics of the 5 drug tests developed are summarized in Table 2. In all 5 cases, the LOQ, i.e. the lower drug concentration on the linear portion of the dose curve, was about 1 decade of concentration higher than the LOD and one decade of concentration lower than the upper limit of the assay, suggesting that the most accurate measurements of the test should be expected at 10-1,000, 1-100, 1-100 and 1-10,000 ng/mL of cocaine, diazepam, amphetamine and methamphetamine concentrations, respectively. However, drugs could be detected in a simple yes/no assay at levels ranging from at least four orders of magnitude to as high as five orders.

TABLE 2

Assay performance characteristics of the 5 drug tests developed

| Assay | LOD ng/ml | LOQ ng/ml | Assay Range ng/ml | Quantitative range ng/ml | % CV |
|---|---|---|---|---|---|
| THC | 0.22 | 1 | 0.22-10,000 | 1-1,000 | 5.0 |
| Cocaine | 1.3 | 10 | 1.3-10,000 | 10-1,000 | 3.9 |
| Diazepam | 0.14 | 1 | 0.14-1,000 | 1-100 | 2.6 |
| D-amphetamine | 0.22 | 1 | 0.22-1,000 | 1-100 | 3.2 |
| Methamphetamine | 1 | 10 | 1-10,000 | 10-8,000 | 4.6 |

Intra-assay precision within the context of the parameters of the LOC system was derived from the degree of agreement of the signals obtained from at least 4 redundant beads within the array, 3.2-4.6% CV for the drugs tests for THC, cocaine/BZE, diazepam, amphetamine and methamphetamine. Inter-assay precision was evaluated using drug standards tested in successive assay runs. This effort revealed inter-assay precision to vary between 4.4-8.0% for the drug based LOC tests for the mid- to high-range drug standard concentrations and 7-15% for the low end of drug standard concentrations.

The accuracy of these tests was assessed in methods comparison studies whereby LOC results from the testing of samples (derived from patients that were administered blind placebos or the fore-mentioned drugs) were compared to those achieved with the gold standard reference method of Liquid Chromatography tandem Mass Spectroscopy (LC-MS/MS), as well as with urine tests completed using commercial immunochromatographic strip (ICS) test kits. A comparison of the three methodologies (BACs, LC-MS/MS and ICS) reveals the advantages offered by the BNC-based tests as developed (Table 3).

The portable BNC tests exhibit exceptional assay performance characteristics with limits of detection (LODs) comparable to the laboratory-confined reference method of LC-MS/MS and vastly superior (significantly lower) than their ICS counterparts. Similar to LC-MS/MS and unlike ICS tests, which are qualitative (Yes/No) type of tests, BNC-based drug tests are fully quantitative. Furthermore, unlike LC-MS/MS which requires tedious sample processing and is limited to testing for one drug at a time, BNC tests are amenable to the point of need, require no extensive sample processing and offer the capacity to multiplex, or test more than one analyte (drug) concurrently, using microliters of sample.

TABLE 3

Comparison of the LOD for three methodologies

| | LC-MS/MS | ICS (urine) | ICS (saliva) | BNC |
|---|---|---|---|---|
| LOD (THC) (ng/mL) | 0.5 | 50 | 50 | 0.2 |
| LOD (diazepam) (ng/mL) | 10 | 300 | 300 | 0.1 |
| LOD (amphetamine) (ng/mL) | 1 | 1,000 | 1,000 | 0.2 |
| LOD (methamphetamine) (ng/mL) | 2.0 | 1,000 | 1,000 | 1.0 |
| LOD (cocaine) (ng/mL) | 2.5 | 300 | 300 | 1.3 |
| Quantitative | YES | NO | NO | YES |
| Portable | NO | YES | YES | YES |
| Multiplexed | NO | LIMITED | LIMITED | YES |

EXAMPLE 2

Expansion of Tests

The proof of concept results were excellent, so the test was expanded so that additional common street drugs could be detected. The reagents chosen after extensive testing for these second generation tests are shown in Table 4. These reagents were tested in a 500 μl bead, multi-assay format and shown to have a dynamic range spanning four to five orders of magnitude with LODs in the ng/ml range, and in many cases less than 1 ng/ml.

TABLE 4

| | | Reagents | | |
|---|---|---|---|---|
| Assay | Optimal Bead Sensor | Catalog # | Tracer | Catalog# |
| THC - format A | BSA-THC (ARISTA) | AGTHC-0304 | THC-SPECIFIC sheep mAb (Randox/Bioventix) | BVX.THC.2B9 |
| THC - format B | THC-SPECIFIC sheep mAb (Randox/Bioventix) | BVX.THC.2B9 | BSA-THC (ARISTA) | AGTHC-0304 |
| Oxazepam | BSA-TEMAZEPAM (Randox) | IMM9552 | BZO-SPECIFIC mouse mAb (ARISTA) | ABBZO-0400 |
| Nordiazepam | BSA-TEMAZEPAM (Randox) | IMM9552 | BZO-SPECIFIC mouse mAb (ARISTA) | ABBZO-0400 |
| Temazepam | BSA-TEMAZEPAM (Randox) | IMM9552 | BZO-SPECIFIC mouse mAb (ARISTA) | ABBZO-0400 |

TABLE 4-continued

Reagents

| Assay | Optimal Bead Sensor | Catalog # | Tracer | Catalog# |
|---|---|---|---|---|
| MDMA | BSA-METH (Randox) | IMM9555 | METH-SPECIFIC sheep mAb (Randox) | PAS10037 |
| MDA | BSA-METH (Randox) | IMM9555 | AMPH-SPECIFIC mouse mAb (ARISTA) | ABAMP-0400 |
| Methadone | BSA-METHADONE (ARISTA) | AGMTD-0303 | METHADONE-SPECIFIC mouse mAb (ARISTA) | ABMTD-0401 |
| Morphine | BSA-MORPHINE (ARISTA) | AGMOR-0300 | MORPHINE-SPECIFIC mouse mAb (ARISTA) | ABMR-0400 |

TABLE 5

Test Data

| Assay | LOD (ng/mL) | LOQ (ng/mL) | Detection Range (ng/mL) | Quantitative Range (ng/mL) | % CV |
|---|---|---|---|---|---|
| THC - format A | 10 | N/A | 10-10,000 | N/A | N/A |
| THC - format B | 1,000 | N/A | 1,000-10,000 | N/A | N/A |
| Oxazepam | 0.97 | 10 | 0.97-100,000 | $10^1$-$10^6$ | 4.8 |
| Nordiazepam | 7.4 | 80 | 7.4-100,000 | 80-100,000 | 13.6 |
| Temazepam | 3.8 | 50 | 3.8-100,000 | 50-100,000 | N/A |
| MDMA | N/A | N/A | N/A | N/A | N/A |
| MDA | 6.7 | 10 | 6.7-1000 | 10-100 | 5.4 at 50 ng/mL |
| Methadone | N/A | N/A | N/A | N/A | N/A |
| Morphine | 0.6 | 2 | 20.6-1000 | 2-100 | 2.3 |

N/A: assay performance characteristics not available yet (work in progress) but proof of concept and assay optimization completed.

Test results to date are shown in Table 5, including optimized results from Example 3.

EXAMPLE 3

THC Optimization

Difficulty in optimizing the THC assay was encountered. In the original reverse competitive immunoformat (immunoformat A or "IFA") the bead-based competitive type of immunoassay was executed as follows: The tracer anti-THC antibody was mixed with the sample and the mixture delivered over a period of 7.5 minutes to the array of beads in the LOC flow cell. The array hosted beads coated with BSA-drug conjugate (i.e. THC-BSA-bead sensors), as well as negative controls beads coated with BSA alone, along with calibrator beads used as internal controls. A reduction in signal indicated that drug in the sample was competing away signal from the drug-bound beads.

However, numerous attempts to further optimize this IFA assay produced minimal improvements in its LOD. As the LOD of the assay is dependent on the intra-assay (or bead to bead) variation for the zero drug (control) condition, the team took a close look at the images of the bead array and discovered the signal around the THC sensitized beads was atypical. Along with the high bead to bead variation in signal intensity, it was noted the signal around the THC-sensitized beads lacked uniformity in shape and was irregular. An attempt to fix the problem by creating a new batch of beads coupled to BSA-THC conjugate produced similar results.

Therefore, reversing the format (immunoformat B or "IFB") was tried. Beads were sensitized to THC via their coupling to the anti-THC antibody (from Randox/Biovendix) and the BSA-THC conjugate was coupled to Alexa Fluor® 488 to serve as the tracer for the assay. This is the typical competitive immunoassay format, but it was not selected initially due to difficulties in conjugating drugs to the label.

THC-Alexa Fluor® 488 was mixed with the sample and the mixture was delivered over a period of 7.5 minutes to the array of beads in the LOC flow cell. Strong and specific binding of the tracer to the anti-THC sensitized beads was quickly demonstrated (not shown). Most importantly, the signal was now more uniform around each bead as well as more consistent with that achieved with other reverse competitive immunoassay format.

Although IFB was an improvement, it was limited to detecting only high concentrations of the drug. The concentration that resulted in competition also exhibited a distortion of the bead integrity when bound to the bead sensors (not shown). The inability to detect lower concentrations of THC was attributed to a sub-optimal tracer, the generation of which is limited to the fact that BSA-THC conjugate (and not THC alone) was used to create the Alexa Fluor® 488-coupled reagent. Noted here, there is currently no known method to couple the Alexa Fluor® 488 directly to the drug, and the BSA or some linker is necessary. Furthermore, the later observation of bead distortion when the anti-THC sensors are exposed to high THC is consistent with the observation of bead distortion associated with IFA, in which case the bead sensors are sensitized to the THC through their coupling to very high THC-BSA concentrations.

In reaction to the observation that high THC on the bead sensors detrimentally affected the bead sensor, whether through the direct or indirect immune-binding, the team reverted back to IFA, with the goal to significantly lower concentrations of THC-BSA. Previous batches of beads were originally loaded with 3 mg/mL of THC-BSA, but later 1 and 0.1 mg/mL THC-BSA levels were tested instead. Loading the beads with lower amounts of THC-BSA significantly improved the signal quality derived from the sensors, as well as benefited the integrity of the sensor (not shown). In fact, the team was able to achieve an LOD of 10 ng/ml using this approach.

It is well known throughout the scientific community that THC represents a challenging target for assay development. Likewise, from all the drugs targeted in this program, THC has been in our experience the most difficult to optimize. The above described "detective" work has resulted in the important observation that THC, when bound at significantly high concentrations on the beads, significantly affects the structural integrity and functional capacity of agarose beads to serve as a sensor for the same drug. Thus, THC-BSA should be loaded at significantly lower levels, as least when coupled to agarose beads.

This is in stark contrast to what is expected, which is the higher the loading, the better the signal. As expected, the bead sensors with lower loading exhibited lower signal intensity in the control (no drug) condition but, more importantly, exhibited significantly less distortion. The reduction in signal intensity may be remedied by increasing the exposure time of the CCD for the optical sensor, and the team is now searching for the optimal condition: one that results to no bead distortion and one that provides the desired signal that may be reduced in response to lower concentrations of THC.

Further optimization steps include exploring functionality of bead sensors loaded with even lower THC-BSA (i.e. 0.01 and 0.001 mg/mL) for IFA, as well as identifying optimal tracer dilution (1:100, 1:500, 1:1000) for the IFA using bead sensors as identified from previous step. It is expected that the LOD can be further improved beyond the 10 ng/ml LOD already demonstrated, to <1 ng/ml.

EXAMPLE 4

Stabilization of Beads

A field environment is likely to be quite different from a lab environment with trained technicians, complex machinery, and optimal working conditions. As one example, in the field, it is likely that the beads may be opened to air, and not used for some time. Therefore, methods of stabilizing the 500 µl beads against drying out were undertaken and glycerol was tested as a preservative or anti-drying agent.

Initial experiments indicated that treatment with 30% glycerol (in PBS) served as an effective method to maintain the moisture around the beads, while likewise maintaining the structural capacity of the beads. The next objective was to determine its effects on their functional capacity as immune sensors on the BNC platform.

Briefly, agarose beads coupled to BSA-THC conjugate were distributed in 5 eppendorf tubes and suspended in 1%, 2%, 10% and 30% glycerol in PBS. Beads were then manually loaded onto the microchip, which was left uncovered and exposed to ambient air, overnight at RT. During that same time period, a fresh bead control (i.e. beads in PBS) was stored at 4° C., until the following day, upon which time beads from this aliquot were also manually loaded on the microchip to complete the array.

The bead-loaded microchip was then quickly sealed in the flow cell, washed with PBS and exposed to anti-THC-Alexa488 coupled tracer and images taken and analyzed. Beads treated with 30% glycerol maintained their structural integrity (shape and size) and performed as well as the fresh bead control. In contrast, air dried beads originally suspended in PBS or in lower concentrations (2 and 10%) of glycerol were reduced in size and, in response to the treatment, failed to produce a tracer-derived signal equivalent to that achieved on fresh beads or beads treated with 30% glycerol.

We also explored the capacity of the glycerol-treated THC bead sensors to respond to the drug in a competition experiment. Data (not shown) indicates that glycerol-treated beads function as well as fresh beads after exposure to the stabilizing agent glycerol, even with real samples in a reverse competitive immunoassay.

We also evaluated the effect of a longer exposure to drying conditions on the performance of the glycerol-treated agarose THC-sensitized beads. In this experiment, beads were treated with 0, 10, 30, 50 and 100% glycerol in PBS and exposed for 5 consecutive days to air, and then compared to fresh beads for their capacity to produce a THC tracer-dependent fluorescent signal. Results suggest that beads treated with 30% or more glycerol were indeed stable and resistant to drying during a 5 day long exposure to drying conditions. Thus, the beads are quite stable to drying in 30% glycerol.

EXAMPLE 5

Bench-Top to Commercial Transition

The drug specific assays are being developed and completed in research grade prototype microfluidic flow cells using 3,000 µl of assay buffer and sample volume. However, reduction of size for the ultimate test will mean less sample is required, and is expected to be completed faster with a short turn-around-time (TAT) of results. Therefore, efforts are underway to reduce the size of the microfluidic lab cards and to fully automate a completely integrated test.

To that end, laminate-based lab cards with integrated sample loading, reaction mixing, buffer washing integrated microfluidics elements were developed and applied for the testing of select drugs. The assays were (or will be) performed as described in Table 6:

TABLE 6

Methodology

General steps to prepare p-BNC components: beads, capture antibody, detection reagents:
    1. Develop bead sensors
    2. Glyoxylate bead sensors
    3. Couple BSA-Drug to the bead sensors (sensitized beads for the specific drug)
    4. Couple BSA to bead sensors (to serve as negative controls)
    5. Couple alexafluor 488 to antibody (to serve as tracer)
    6. Add sodium azide to the bead solution (to prevent bacterial contamination)

TABLE 6-continued

Methodology

7. In some iterations, add glycerol (to prevent drying of bead sensors/i.e. promote stability)
  8. Store bead sensors at 4° C. until use.
  9. Aliquot tracer-alexa488 in assay-relevant volumes (it varies from drug to drug)
 10. Store alexafluor488a aliquots at −20° C. until use.
 11. Prepare calibrator beads by coupling them to an irrelevant to the assay antibody-coupled toalexafluor488.
 12. For laboratory-based measurements, prepare re-usable flow cells (lab cards)
 13. For on-site measurements use mass-produced integrated lab card Sample collection
  1. Saliva may be collected either as expectorated specimen or via a saliva collection device, such as: Aware Messenger or Quantisal
  2. Once sample is collected it may be tested promptly or aliquoted in assay relevant volumes (200-400 µL) stored frozen until the day of the test.

Prepare serial dilutions of drug standards (typically, 0, 0.01, 0.1, 10, 100, 1,000 and 10,000 ng/mL)
  1. For laboratory-based measurements, store aliquoted solutions of drug standards at −20° C. until use.
  2. For on-site measurements, standards will be provided as a part of the kit in lyophilized form along with stabilizers, until use. The kits are expected to be stored at 4° C. for up to 1 year, or at room temperature (i.e. 25° C.) for up to 1 week or at 37° C. for up to 48 hrs.

Assay principle:
The bead-based competitive type of immunoassay is executed as follows: The tracer antibody is mixed with the sample and the mixture is delivered over a period of 7.5 minutes to the array of beads in the LOC flow cell or lab card. The array hosts beads coated with BSA-drug conjugate, as well as negative controls beads coated with BSA alone, along with calibrator beads used as internal controls. In the absence of drug in the sample, the tracer antibody will efficiently recognize and bind to the bead sensors for which it is specific (coated with the drug of interest) and thus produce a fluorescent signal within and around the bead; in the presence of drug in the sample, which will compete with the drug on the bead for binding to the tracer, the signal on the bead loaded with BSA-drug will be reduced in a dose-dependent manner.

For laboratory-based measurements, use re-usable flow cells/lab cards & complete assay sequence, as follows:
  1. Manually load drug-sensor beads, negative control beads, and calibrator beads in addressable positions within the array.
  2. Seal the flow cell.
  3. Place flow cell under the fluorescent microscope.
  4. Connect flow cell to fluidic lines
  5. Deliver PBS buffer to wet the array
  6. Pre-mix sample (500 µL of either drug standard for the dose curve or unknown sample) with assay buffer (PBS) (2500 µL) for a total of 3 mL
  7. Add tracer (amount varies from 1-25 µL depending on the assay/drug), mix and start the timer.
  8. Promptly deliver assay buffer/sample/tracer mixture to the array for 7.5 minutes.
  9. PBS wash for 2 minutes directs unused reagents to waste.
 10. Assay sequence is completed with PBS wash.
 11. Image of bead array is captured at various CCD exposure settings
 12. Data from the testing of the standards and of the unknown samples are processed to build dose response curves and to establish the measurement of the unknowns. Here multiple dose curves are generated at the various CCD exposures, the best (based on LOD and assay range) of which (one exposure alone or in combination for a wider range) is selected for the prediction of the samples tested For on-site measurements, use integrated lab card:
Mass produced integrated lab cards will be offered as part of an assay kit that will include the following:
  1. Integrated lab card with pre-loaded:
        a. Bead support (microchip)
        b. Bead sensors for drugs, negative control beads, and calibrator beads in addressable positions within the array on the microchip
  2. In one iteration, the tracer antibody will be pro-loaded and dried on pads along with stabilizers in a dedicated position within the microfluidic circuitry of the integrated card.
  3. Self-contained bio-waste compartment
  4. Oral Fluid Sample Collection device consisting of an oral fluid collection swab, and a tube with analyte extraction fluid, and a cap #1 to seal the tube.
  5. In another iteration, the tracer antibody will be integrated within a second cap (#2) fitting the sample collection device. The cap will be equipped with a filter membrane with tracer present in dried/stabilized form on the membrane.
  6. Drug standards for the generation of dose curve.
  7. Quality controls
  8. Instruction manual Test sequence: with tracer antibody on the cap of the collection vial
  1. Collect sample using the oral swab
  2. Extract analyte from swab by dipping it in and out of the extraction buffer
  3. Remove and discard collection swab
  4. Seal the tube with cap#2. Invert tube to allow reconstitution of the dried tracer and mix. Timer starts now.
  5. Promptly load sample-tracer mixture on the loading site of the integrated card.

TABLE 6-continued

Methodology

9. Insert the card into the analyzer.
10. Analyzer will execute the following steps:
    a. Promptly deliver assay buffer/sample/tracer mixture to the array for 7.5 minutes.
    b. Upon completion of the 7.5 minute period, a PBS wash for 2 minutes directs unused reagents to waste.
    c. Assay sequence is completed with a PBS wash.
11. Image of bead array is captured at various CCD exposure settings
12. Data from the testing of the standards and of the unknown samples are processed to build dose response curves and to establish the measurement of the unknowns. Here multiple dose curves are generated at the various CCD exposures, the best (based on LOD and assay range) of which (one exposure alone or in combination for a wider range) is selected for the prediction of the samples tested.

Test sequence: with tracer antibody dried on a pad within the integrated lab card
1. Collect sample using the oral swab
2. Extract analyte from swab by dipping it in and out of the extraction buffer
3. Remove and discard collection swab
4. Load sample (200-400 µL) on the loading site of the integrated card.
5. Insert the card into the analyzer.
6. Analyzer will execute the following steps:
    a. Promptly deliver sample to the tracer pad
    b. Tracer will be reconstituted by the sample and the two will be mixed within a mixing chamber within the lab card en route to the bead array. Assay timer is initiated as soon as sample/tracer mixture reach the mixing chamber.
7. Upon completion of the 7.5 minute period, a PBS wash for 2 minutes directs unused reagents to waste.
8. Assay sequence is completed with PBS wash.
9. Image of bead array is captured at various CCD exposure settings
10. Data from the testing of the standards and of the unknown samples are processed to build dose response curves and to establish the measurement of the unknowns. Here multiple dose curves are generated at the various CCD exposures, the best (based on LOD and assay range) of which (one exposure alone or in combination for a wider range) is selected for the prediction of the samples tested.

Proof of concept for integrated test for the drug oxazepam has been achieved. Noted are the following performance characteristics for this test:

1. Reduced assay time (from 10 minutes down to 2 minutes).
2. Reduced assay volume requirement (from 3 mLs down to 0.4 mLs).
3. High intra-assay precision (very low bead to bead variation).
4. No apparent sacrifice in analytical performance (i.e. still a significant reduction of signal in competition mode).
5. In contrast to the macroscale counterparts, which are re-usable, these novel microscale structures are single-use and disposable.

The lab-based assay must be further optimized for field use, especially as regards sample collection and test procedures. To that end we are testing a variety of field formats, including use of commercially available swab tests for sample collection. These commercially available cheek swab kits have tested as better and more reproducable than just collecting expectorant. Thus, we anticipate that standard swabs will be packaged with the kit, and including a vial of PBS or other suitable sample extraction buffer for collecting the sample off the swab and solubilizing it.

The tracer can be applied in various ways. It can added by the user to the sample buffer or be kept in dried form in a separate cap to be added to the sample buffer once the swab is washed in the buffer. Alternatively, it can be contained in a reagent blister or in a dried reagent pad in the fluidic pathway. It is expected that this third alternative will be the most user friendly, however, all methods will be tested. Of course, the stability of dried reagent will have to be assessed, but dried antibodies are already extensively used in home testing kits and are known to be reliable and long lasting.

We will also test various kits formats. Two capped vials is one option—one vial holding the sterile swab, and the other containing wash buffer. The swab is pulled from the first vial, swished in the second buffer-containing vial and the resulting sample is then applied to the cartridge. To that end, the swab end can also comprise an inexpensive plastic dropper (like an eye dropper), as is already known in the art, thus facilitating transfer from the buffer vial to the cartridge.

We will also test a compartmentalized single vial system, wherein the buffer is separated from the swab by a layer of material that is easily pierced by the user. Thus, the swab is removed from the dry portion of the vial, a saliva sample collected, and when returned to the vial at a slightly greater depth, the layer is pierced, and the buffer washes the sample off the swab. The sample is then transferred to the cartridge via e.g., an eye dropper.

FIG. 3A-D shows this embodiment comprising a top 1 in FIG. 3A and vial 21 in 3B, shown in a storage position in 3C and in wash position in 3D. The top is a combination of eye dropper, cap and swab, preferably made of lightweight flexible plastic, wherein the bulb portion and cap ridges have more flexibility (higher durometer or thinner) than the remaining portions. The vial has a sheet of flexible foil or plastic separating wash buffer in the lower wash portion of the vial from the upper storage portion of the vial. The sizes shown in FIG. 3 are approximate only, and the exact proportions will have to be calibrated to allow washing of the swab without overflowing or contaminating the buffer.

In more detail, top 1 comprises a bulb 11, and cap 12, having optional annular flexible ridges or protrusions 13 for sealing the cap inside the vial 21. Bulb 11 is fluidly connected via hollow stem 14 to open point 16 and has an absorbent or bristled swab 15 on the outer surface of stem 14.

Vial 21 consists of a container 22 having a foil or plastic separator 24 to separate buffer 25 from the upper portion of the container 22. Optional ledge 23 can be included to prevent the top 1 from being pushed too far into the vial 1, but this may not be needed, since the length of top 1 can effectively control this as well. Ledge 23 can be annular, that is circumnavigate the container, or can just be two or more smaller steps roughly equi-spaced, as desired. We have shown a cylindrical container, but any shape is possible. It may be preferred that container have a flat bottom (not shown) to allow it to stand on its own during assemble and use.

In the closed position shown in FIG. 3C, the cap 12 seals the container via flexible ridges 13, keeping swab 15 sterile and above separator 24 in the upper storage portion of the vial. In use, the top is removed, and the swab used to collect saliva samples from a suspect. The top 1 is then returned to the vial 21 in FIG. 3D, pushing point 16 past the separator 24, thus rupturing it, and allowing the user to wash the swab 15 in buffer 25. When sufficiently washed (maybe 4-5dunks), the bulb 11 is squeezed and released, thus drawing buffer 25 up into the bulb 11 via open point 16 and hollow stem 14. This wash and sample buffer can then be applied to the cartridge. The device can be recapped and saved, or thrown away, according to standard protocols.

Figure 4A:
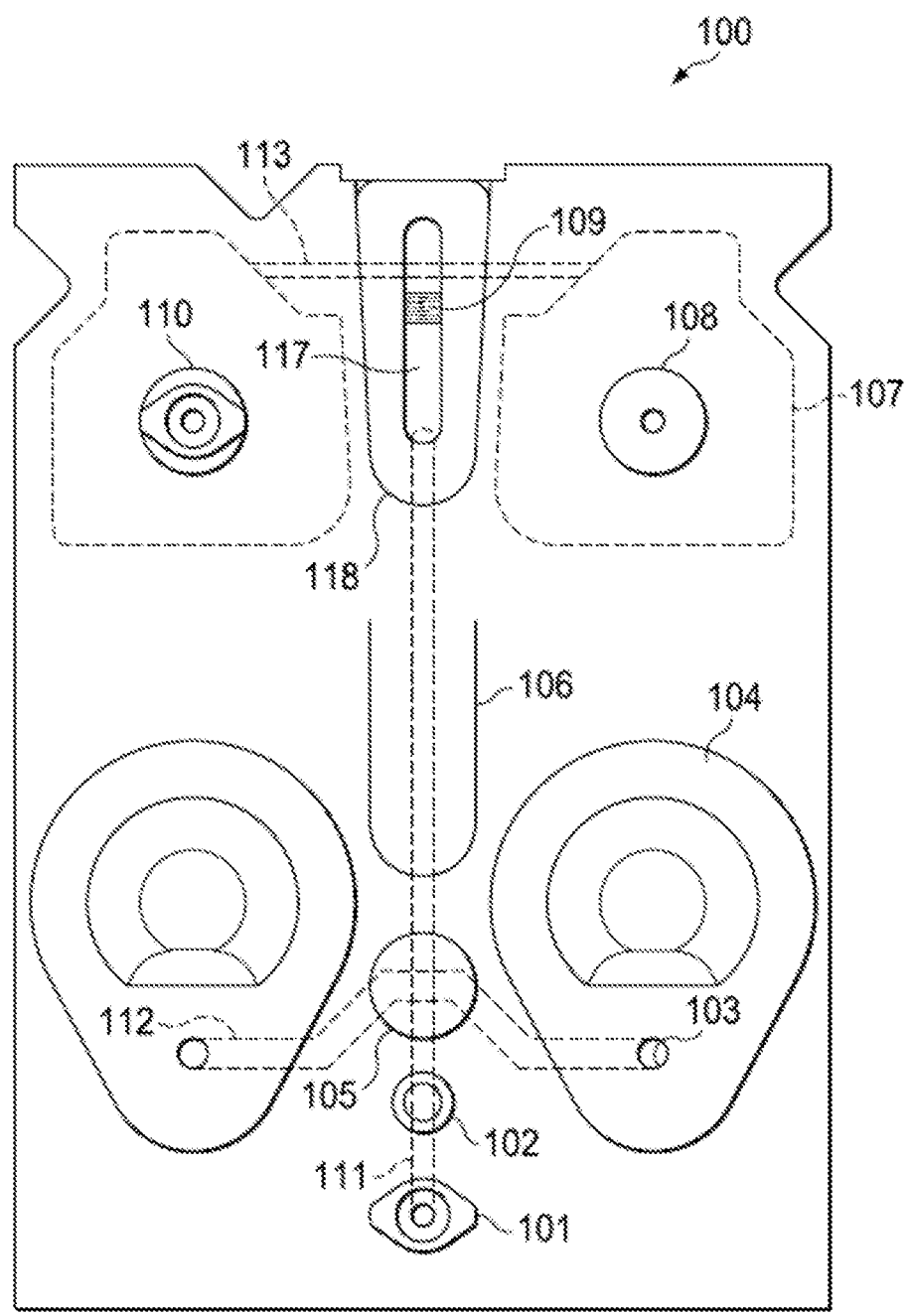
FIG. 4A-B shows a top plan view 4A of the cartridge, and a perspective view 4B showing details of a preferred access hatch construction.
Figure 4B:
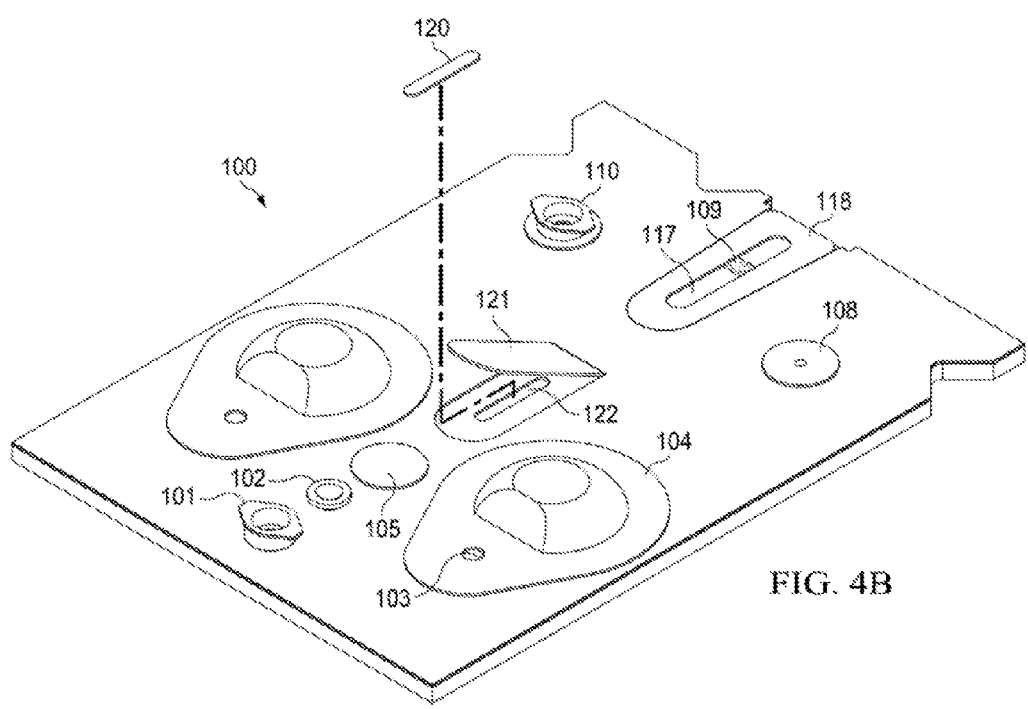

The BNC cartridge itself will also be contained inside a sterile, airtight wrapper, probably foil (not shown). It is opened when needed, sample applied either via the cartridge or via a fluidly connected port on the reader, dropped into a portable detector, and the test run. FIG. 4A-B show an exemplary cartridge, which is disposable and fits into a standard reader.

In more detail, 101 is the sample entry port, which is fluidly connected via microfluidics 111 to the bead support chip chamber 117. A small array of bead sensors (see black square 109) fits inside this chamber, which has a transparent lid 118. Pinch valve 102 functions to allow controlled delivery of microfluidic elements. Buffer entry ports 103 are fluidly connected 112 to microfluidic channel 111. One, two or more blister packs 104 can contain liquid reagents, such as wash buffers. Alternatively, the device could be connected directly to an external fluid source via buffer entry ports 103, but the blister packs are preferred as being more self-contained and providing a smaller footprint. The blisters are accessed via pressure actuation, a function provided by the analyzer/reader and embedded software, and thus are preferably foil blisters.

Bubble trap 105 allows for pressure relief, otherwise the fluid would not flow in the tiny channels. Alternatively, waste chambers 110 can be closed under negative pressure and thus pull fluid in their direction when a valve is opened.

Reagent port 106 can contain an absorbent pad 120 (see perspective inset 4B) having dried reagents (labeled antibody-tracer) thereon. Thus reagent port 106 can consist of an access hatch or affixed cover 121 and recess 122, into which reagent pad 120 can be placed. Alternatively, reagent port 106 could be another blister pack or again just an inlet allowing connection to external fluids. Waste reservoir 107 and waste reservoir external vent 108 are also fluidly connected via microfluidic channel 113 to assay chamber 117 having a transparent access hatch or affixed cover 118 allowing visual access to the bead array, but keeping the beads airtight. Optional port to waste chamber 110 is also shown, although the chamber can be made sufficiently large to hold all waste and this port omitted.

In preferred embodiments, disposable plastic chip containing the microfluidics is made by injection molding and/or etching of parts and adhering layers together. Access hatch 121 (shown open) at recess 122 and access hatch 118 (shown closed) at recess 117 allow the insertion of the bead array 109 and reagent pad 120, and can then be closed and tightly sealed, e.g., with heat or adhesive. Blisters are added via adhesive strip.

Preferred materials for constructing the cartridge are plastics of durometer 34-40 Shore D for the substrate and microfluidics, such as polymers and copolymers of styrene, acrylic, carbonate, butadiene, propylene, vinyl, acrylonitrile, and foil for the blisters.

We envision that a detector will be designed and manufactured specifically for this assay, as this will allow simplification of the device and its software, and minimization of the footprint. Ideally, the device will be reduced to a hand held size, and thus be easy for police officers to use in road-side testing environments. The analyzer (aka reader or detector) serves as a universal interface, providing the user with access to a fully embedded software, and components needed to run the assay, read the results, and convert the data to a user friendly output.

The analyzer is composed of i) lab card loading deck, ii) optics, iii) charged coupled device (CCD camera) or other light measuring means, iv) software, vi) mechanical actuators for movement of microfluidics (e.g., needle for piercing blister packs and means for moving/actuating same), vii) pump, and viii) data output (e.g., paper and printer), and/or USB port and/or display means and ix) data input means.

In use, the officer inputs the suspects name and any other pertinent information, collects and applies the sample, presses a start button, and the device runs the tests and outputs the answers.

We are also experimenting with the best method of calibrating the data for quantitative use, although the system is ready for use in a yes/no format. One option is to calibrate the instrument daily before actual field use. Thus, the Officer can apply known standards cartridge to the device and calibrate the device before actual use on suspects in the field. It may also be that daily calibration is not needed, and that weekly calibration or less may suffice, and assay drift over time will be assessed. Another option is to provide separate fluidics (double the fluidics) so that standards and samples can be tested at the same time.

The following references are incorporated herein in their entireties by reference, for all purposes.

US20050214863
US2006257941
US2006257991
US2006257992
US2006257993
US2008300798
US2008219891
US20100291588
US2011251075
U.S. Pat. No. 6,649,403
U.S. Pat. No. 6,713,298
U.S. Pat. No. 7,651,868
U.S. Pat. No. 7,491,552
U.S. Pat. No. 7,316,899
WO2007002480
WO2005083423
WO2005085855

Aps J K & Martens L C Review: The physiology of saliva and transfer of drugs into saliva, Forensic Sci Int 150: 119-131 (2005).

Blencowe T, et al, An analytical evaluation of eight on-site oral fluid drug screening devices using laboratory confirmation results from oral fluid, Forensic Science International 208:173-179 (2011).

Blencowe T, et al., An analytical evaluation of eight on-site oral fluid drug screening devices using laboratory confirmation results from oral fluid. Forensic Science International 208: 73-179 (2011).

Bosker W M & Huestis M A, Oral Fluid Testing for Drugs of Abuse, Clin. Chem. 55: 1910-1931 (2009).

Choo R E, Huestis M A. Oral fluid as a diagnostic tool, Clin Chem Lab Med 42(11):1273-1287 (2004).

Christodoulides N, et al. Application of microchip assay system for the measurement of C-reactive protein in human saliva. Lab Chip 5(3):261-69 (2005).

Christodoulides N, et al., Lab on a chip Methods for Point of Care Measurements of Salivary Biomarkers of Periodontitis, Ann. N.Y. Acad. Sciences 1098:411-428 (2007).

Cone E J, Saliva testing for drugs of abuse, Ann N Y Acad Sci 694: 91-127 (1993).

Drummer O H, Introduction and review of collection techniques and applications of drug testing of oral fluid, Therapeutic Drug Monitoring 30: 203-206 (2008).

Drummer O H, Review: Pharmacokinetics of illicit drugs in oral fluid Forensic Science International 150: 133-142 (2005).

Floriano P N, et al. Use of saliva-based nano-biochip tests for acute myocardial infarction at the point of care: a feasibility study, Clin Chem. 55(8):1530-38 (2009).

Gorodetzky C W & Kullberg M P, Validity of screening methods for drugs of abuse in biological fluids. II. Heroin in plasma and saliva, Clinical Pharmacology & Therapeutics 15: 579-587 (1974).

Idowu O R & Caddy B, A Review of the Use of Saliva in the Forensic Detection of Drugs and Other Chemicals. J Forensic Science Society 22: 123-135 (1982).

Jokerst J, et al., Programmable Nano-Bio-Chip Sensors: Analytical Meets Clinical. Anal Chem. 82:1571-79 (2010).

Jokerst J V, et al. Nano-bio-chips for high performance multiplexed protein detection: Determinations of cancer biomarkers in serum and saliva using quantum dot bioconjugate labels, Biosens Bioelectron. 24:3622-29 (2009).

Kaufman E & Lamster I B, The diagnostic application of saliva—A review, Crit Rev Oral Biol Med 13: 197-212 (2002).

Lillsunde P, Analytical techniques for drug detection in oral fluid, Therapeutic Drug Monitoring 30: 181-187 (2008).

Melanson S E F, Drug-of-Abuse Testing at the Point of Care, Clinics in Laboratory Medicine 29: 503 (2009).

Riet D R, et al., Oral Fluid as an Alternative Matrix to Monitor Opiate and Cocaine Use in Substance-Abuse Treatment Patients, Drug Alcohol Depend, 87(2-3): 258-267 (2007).

Rifai N & Ridker P M, High-Sensitivity C-Reactive Protein: A Novel and Promising Marker of Coronary Heart Disease, Clin Chem 47: 403-411 (2001).

Scheidweiler K B et al., Pharmacokinetics of Cocaine and Metabolites in Human Oral Fluid and Correlation With Plasma Concentrations After Controlled Administration. Ther Drug Monit 32(5): 628-637 (2010).

Schepers R J F, et al., Methamphetamine and Amphetamine Pharmacokinetics in Oral Fluid and Plasma after Controlled Oral Methamphetamine Administration to Human Volunteers, Clinical Chemistry 49:1, 121-132 (2003).

Schramm W, et al., Drugs of Abuse in Saliva—a Review, J Analytical Toxicology 16: 1-9 (1992).

Svojanovsky SR, et al., High sensitivity ELISA determination of taxol in various human biological fluids, J Pharm Biomed Anal 20: 549-555 (1999).

Toennes S W, et al., Driving under the influence of drugs—evaluation of analytical data of drugs in oral fluid, serum and urine, and correlation with impairment symptoms, Forensic Sci Int 152: 149-155 (2005).

Van Bocxlaer J F, et al., Liquid chromatography-mass spectrometry in forensic toxicology, Mass Spectrometry Reviews 19: 165-214 (2000).

Walsh J M, et al., An evaluation of rapid point-of-collection oral fluid drug-testing devices, J Anal Toxicol 27: 429-439 (2003).

Yeh C K, et al., Current development of saliva/oral fluid-based diagnostics, Tex Dent J. 127(7):651-61 (2010). Review.

The invention claimed is:

1. A drug testing device comprising:
   a microfluidic lab-on-chip based reverse competitive immunoassay system comprising a disposable cartridge and a separate reader, wherein said cartridge fits into a slot on said reader, and said reader is configured to perform a reverse competitive immunoassay using said cartridge and output a result;
   said cartridge comprising:
   i. a generally flat substrate having embedded microfluidic channels connecting an inlet port to an embedded downstream assay chamber having a transparent cover and containing a removable array of bead sensors,
   ii. one or more reagent chambers fluidly connected to and upstream of said assay chamber, and
   iii. one or more waste fluid chambers fluidly connected to and downstream of said assay chamber,
   wherein each bead sensor is a porous polymeric bead of size between 50-300 μm±10% having a drug conjugated thereto, wherein said drug is selected from three or more of THC, diazepam, oxazepam, nordiazepam, temazepam, D-amphetamine, methamphetamine, methadone, morphine, MDA, MDMA and biological metabolites of same;
   wherein said reverse competitive immunoassay has a lower limit of detection for each of said drugs of <10 ng/ml and a detection range of at least four orders of magnitude; and
   wherein each said bead sensor is pre-treated with glycerol.

2. The drug testing device of claim 1, said cartridge comprising 4 or more of said drugs.

3. The drug testing device of claim 1, said cartridge comprising each of said drugs.

4. The drug testing device of claim 1, wherein each said bead sensor is pre-suspended in 30% glycerol in PBS.

* * * * *